(12) United States Patent
Claus

(10) Patent No.: US 7,126,351 B2
(45) Date of Patent: Oct. 24, 2006

(54) METHOD AND DEVICE FOR DISTINGUISHING GEM STONES

(75) Inventor: Patrick Claus, Vinderhoule (BE)

(73) Assignee: Wetenschappelljk en Technisch Onderzoekscentrum voor Diamant Inrichting erkend bij toepassing van de besluitwet van 30 januari 1947, Lier (BE)

(*) Notice: Subject to any disclaimer, the term of this patent is extended or adjusted under 35 U.S.C. 154(b) by 0 days.

(21) Appl. No.: 10/612,392

(22) Filed: Jul. 3, 2003

(65) Prior Publication Data

US 2005/0068047 A1    Mar. 31, 2005

(30) Foreign Application Priority Data

Jul. 5, 2002 (BE) ................... 2002/0427

(51) Int. Cl.
*G01R 27/26* (2006.01)

(52) U.S. Cl. ...................... 324/663; 324/687

(58) Field of Classification Search ............... 49/360; 324/663, 698, 717, 687
See application file for complete search history.

(56) References Cited

U.S. PATENT DOCUMENTS

| | | | |
|---|---|---|---|
| 3,864,626 A * | 2/1975 | MacLean et al. ........... 324/663 |
| 4,255,962 A | 3/1981 | Ashman | |
| 4,324,129 A | 4/1982 | Goldsmid | |
| 4,344,315 A | 8/1982 | Moxon et al. | |
| 4,616,939 A | 10/1986 | Gitlis | |
| 4,710,550 A * | 12/1987 | Kranbuehl ................... 526/60 |
| 5,379,102 A | 1/1995 | Takeuchi | |
| 5,559,436 A | 9/1996 | Matthews et al. | |
| 5,882,786 A | 3/1999 | Nassau et al. | |
| 5,955,735 A | 9/1999 | Coleman | |
| 6,043,742 A | 3/2000 | Austin | |
| 6,265,884 B1 | 7/2001 | Menashi et al. | |
| 2004/0239305 A1 * | 12/2004 | Clauss et al. ................. 324/67 |

FOREIGN PATENT DOCUMENTS

| | | |
|---|---|---|
| EP | 0424167 | 4/1991 |
| GB | 267462 | 9/1927 |

* cited by examiner

*Primary Examiner*—Walter Benson
(74) *Attorney, Agent, or Firm*—Browdy and Neimark, PLLC

(57) ABSTRACT

Natural diamonds can be discerned from imitations, synthetic diamonds and treated diamonds on the basis of their physical qualities. Labs always test several specific characteristics in order to discern natural diamonds from others. One of the tested qualities is electrical conductivity. The invention concerns a method to establish the presence of electrical bulk conductivity. Use is made to this end of the fact that the proximity of an electrically conductive object (gemstone) has an influence on the parasitic capacity of a capacitive probe. The parasitic capacity is also influenced by the dielectric constant of the dielectric. The influence of the proximity of electrically conductive gemstones as opposed to non-conductive gemstones on the parasitic capacity is hereby larger than the influence of the differences in the dielectric constant of the gemstones.

15 Claims, 3 Drawing Sheets

METHOD AND DEVICE FOR DISTINGUISHING GEM STONES

The invention concerns a method and device for qualifying gemstones, whereby gemstones are discerned from one another on the basis of their electrical conductivity characteristics. In particular, the invention relates to the distinction of gemstones which are not electrically conductive as opposed to synthetic or thermally treated gemstones.

According to the present state of the art, gemstones are discerned from one another on the basis of differences relating to one or several physical characteristics such as, among others, optical transmission, thermal conductivity, electrical conductivity or specific gravity.

Thus, for example, silicon carbide, also known as moissanite, and other synthetic stones can be discerned from diamonds thanks to the differences in electrical and thermal conductivity.

The major part of all diamonds, i.e. type I and most type IIa diamonds, have a high electrical resistance which exceeds $10^{14}$ ohm m. Type IIb diamonds, characterised by boron substitution in the crystal and a typically blue colour when the concentration of boron is sufficiently high, have a low electrical resistance of $10^{-1}$ to 100 ohm m.

Certain synthetic or treated gemstones cannot be discerned from natural gemstones with the existing methods.

U.S. Pat. No. 5,882,786 describes for example a gemstone whereby a moissanite core is coated with a thin diamond layer. Existing methods, such as described for example in U.S. Pat. No. 6,265,884, will classify this gemstone as a natural diamond, since the electrical contact resistance of the outer surface of the gemstone is measured with a probe with these methods.

Diamonds of a low quality can be treated at high temperatures, which results in a diamond with a black colour due to graphitisation. In the case of a diamond gem with macro crystals showing many fractures, this formation of graphite will be concentrated around said fractures which reach up to the surface of the gemstone. Consequently, when the electrical conductivity is measured through contact with the surface of the gemstone, the measuring result will depend on the position of the measuring points. In fracture-free spots, the gemstone will be non-conductive, whereas it is conductive indeed at the height of the fractures.

In the case of a high-temperature treatment of a polycrystalline diamond with individual crystals which are smaller than 1 µm, there will be an internal colouring or bulk colouring, as a result of which the gemstone turns opaque black due to the transformation of diamond in graphite and amorphous carbon. The surface of the gemstone as well as the inside hereby become electrically conductive. After re-cutting or "deep-boiling", the surface conductivity will disappear, whereas the inner electrical conductivity is maintained.

U.S. Pat. No. 5,955,735 describes a method whereby an electric potential is measured when a moissanite gemstone is exposed to ultraviolet light. Although, in principle, this method does not require that the gem is not set, an electrical contact has to be made with it. For gemstones coated with diamond, the electric potential cannot be measured, and the method fails.

U.S. Pat. No. 4,255,962, U.S. Pat. No. 4,344,315, U.S. Pat. No. 4,324,129, U.S. Pat. No. 4,616,939 describe test arrangements based on the thermal conductivity of the gemstones. For diamond-coated gemstones and gemstones having a thermal conductivity comparable to that of diamonds, such as for example moissanite, these methods fail.

The invention aims to remedy these disadvantages by providing a method and a device which make it possible to discern gemstones in a simple and reliable manner, based on the electric characteristics of the gemstone, whereby gemstones having an internal conductivity as well as gemstones having an electrical conductivity at their surfaces can be qualified.

To this aim, at least a part of a gemstone which needs to be qualified is placed in the electrical field of a capacitor, whereby the electrical capacity of this capacitor is measured and compared to a reference capacity of said capacitor when reference material having a high relative dielectric constant is placed in said electrical field, whereby said gemstone is qualified as a gemstone with electrical conductivity qualities when the measured capacity of said capacitor, containing the above-mentioned part of the gemstone, is larger than said reference capacity. The relative permittivity of the aforesaid reference material is hereby preferably larger than that of the gemstone to be qualified.

Practically, before said reference capacity is measured, a reference material is used having a dielectric constant which is larger than 9.7. Consequently, for all gemstones that are not electrically conductive, having a dielectric constant which is smaller than 9.7, the measured capacity will be lower than said reference capacity.

In an advantageous manner, in order to measure said capacity, or said reference capacity, the gemstone to be qualified, or said reference material, is placed in the electrical stray field of said capacitor.

In a particularly advantageous manner, said part of the gemstone to be qualified, or said reference material respectively, is put in the measuring range of a capacitive measuring probe in order to measure said capacity, or said reference capacity.

The invention also concerns a device for qualifying gemstones in order to discern natural gemstones from imitations, such as synthetic or thermally treated gemstones, whereby this device comprises a capacitor which makes it possible to place at least a part of the gemstone to be qualified in the electrical field thereof. This device is further equipped with a read-out unit and a measurement converter which generates a signal as a function of the capacity of said capacitor, whereby this signal is displayed via said read-out unit.

According to a preferred embodiment of the device according to the invention, said capacitor has an electrical stray field whereby said gemstone can be placed in this stray field.

Preferably, the capacitor comprises a capacitive measuring probe which is provided, for example, with two concentric cylindrical electrodes.

According to a special embodiment of the device according to the invention, the electrodes of said capacitor are electrically shielded in order to make sure that its electrical stray field cannot be disturbed by conductive parts of a jewel in which the gemstone to be qualified is set.

Other particularities and advantages of the invention will become clear from the following description of an embodiment of the method and device according to the invention; this description is given as an example only and does not restrict the scope of the claimed protection in any way; the figures of reference used hereafter refer to the accompanying drawings.

In the different drawings, the same reference figures refer to identical or analogous elements.

The method and device according to the invention aim to discern gemstones on the basis of their electrical conductivity. The method makes it possible to detect the external electrical conductivity or surface conductivity, as well as the internal electrical conductivity or the bulk conductivity of the gemstone.

Figure 1:
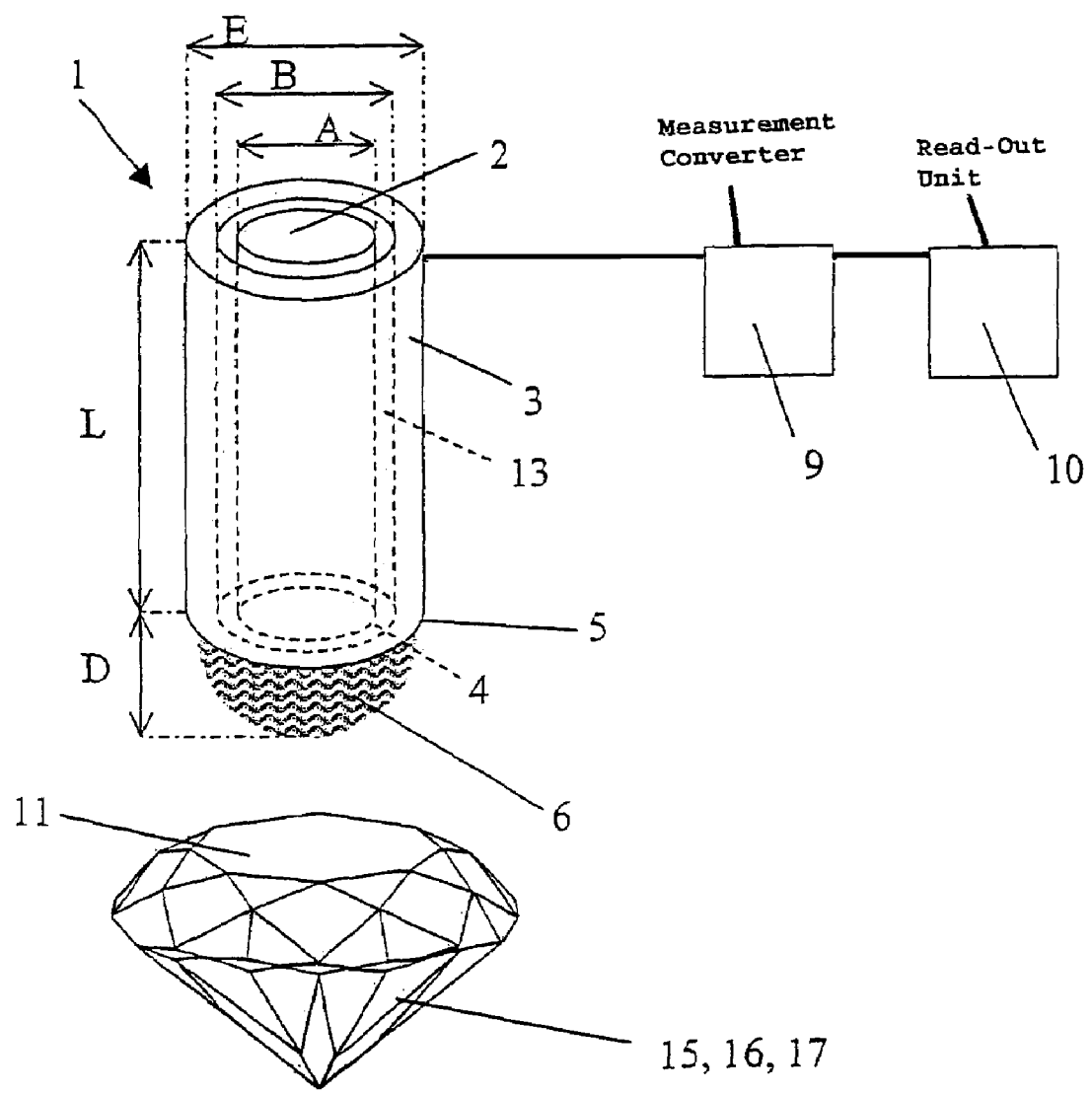
FIG. 1 is a schematic representation of a gemstone and a capacitive measuring probe with a measurement converter and a read-out unit.

According to a first embodiment of the method according to the invention, use is made of a capacitive measuring probe 1 as represented in FIG. 1.

This measuring probe 1 comprises two electrodes 2 and 3 which are formed of two electrically conductive concentric cylinders 2 and 3 with a length L and a radius a, b respectively. The electrodes 2 and 3 are electrically separated from one another by a non-conductive medium 13 and they form a capacitor whose basic capacity $C_0 = 2\pi \in_0 \in_r L / \ln(b/a)$, whereby $\in_0$ is the absolute permittivity. $\in_r$ represents the relative permittivity of the dielectric constant of the medium 13.

When an electrical field is generated between these electrodes 2 and 3, an electrical stray field 6 is created on the outer edges 4 and 5 thereof which gives rise to a parasitic capacity $C_p$. The parasitic capacity $C_p$ depends on the construction of the capacitor and the environmental characteristics. The total capacity equals the sum of the basic capacity and the parasitic capacity, $C_t = C_0 + C_p$.

An object, such as a gemstone 15, 16, 17, situated in the electrical stray field 6 of the capacitive probe 1, has an influence on its parasitic capacity. This parasitic capacity is influenced only to a limited extent by the dielectric constant of the object situated in this electrical stray field 6. However, the influence of an object with electrical conductivity qualities on the parasitic capacity is relatively important. This influence is inversely proportionate to the distance between the probe and the object with electrical conductivity qualities.

Consequently, when different gemstones are successively placed in the stray field of the parasitic capacity, it is found that a difference in electrical conductivity of the gemstones has a larger influence on the parasitic capacity than a difference in the dielectric constant of the gemstones. In particular, the influence of the difference in the dielectric constant of different gemstones on the capacity of the capacitive probe can practically be neglected when compared to the influence of the difference in the electrical conductivity thereof.

The active electrical stray field 6 of the capacitive probe 1 consists of bent flux lines 8 extending between both electrodes 2 and 3. By active flux lines 8 are meant all electrical flux lines 8 which contribute to the measuring range of the capacitive measuring probe 1. The geometry and the dimensions of the electrodes 2 and 3 and the sensitivity and measuring range of a measurement converter 9 which is connected to the measuring probe 1 determine the extent of the active flux lines 8. The height D of the electrical stray field 6 is defined by the maximum distance between a very active flux line 8 and the plane comprising the outer edges of the electrodes 2 and 3. This latter plane forms what is called a measuring plane. The height D thus corresponds to the detection depth of the measuring probe 1.

The measurement converter 9 creates an output signal which depends on the capacity of the capacitor of the measuring probe 1. This output signal is not necessarily linear in relation to the total capacity, the parasitic capacity or any physical quantity whatsoever influencing the capacity. Further, a read-out unit 10 has been provided which makes it possible to register the output signal.

The electrodes 2 and 3 are made such that the parasitic capacity $C_p$ is large in relation to the basic capacity $C_0$. Consequently, the environment of the capacitor will have a strong influence on the total capacity $C_t$. In particular, a change in the conductivity or relative dielectric constant $\in_r$ of the medium at the electrical stray field 6 will strongly influence the total capacity $C_t$. By bringing a solid matter in the electrical stray field 6, the total capacity $C_t$ is altered.

Most solid matters have a relative dielectric constant $\in_r$ between 2 and 10. Thus, $\in_r = 5.7$ for diamonds and $\in_r = 9.7$ for moissanite.

Figure 2:
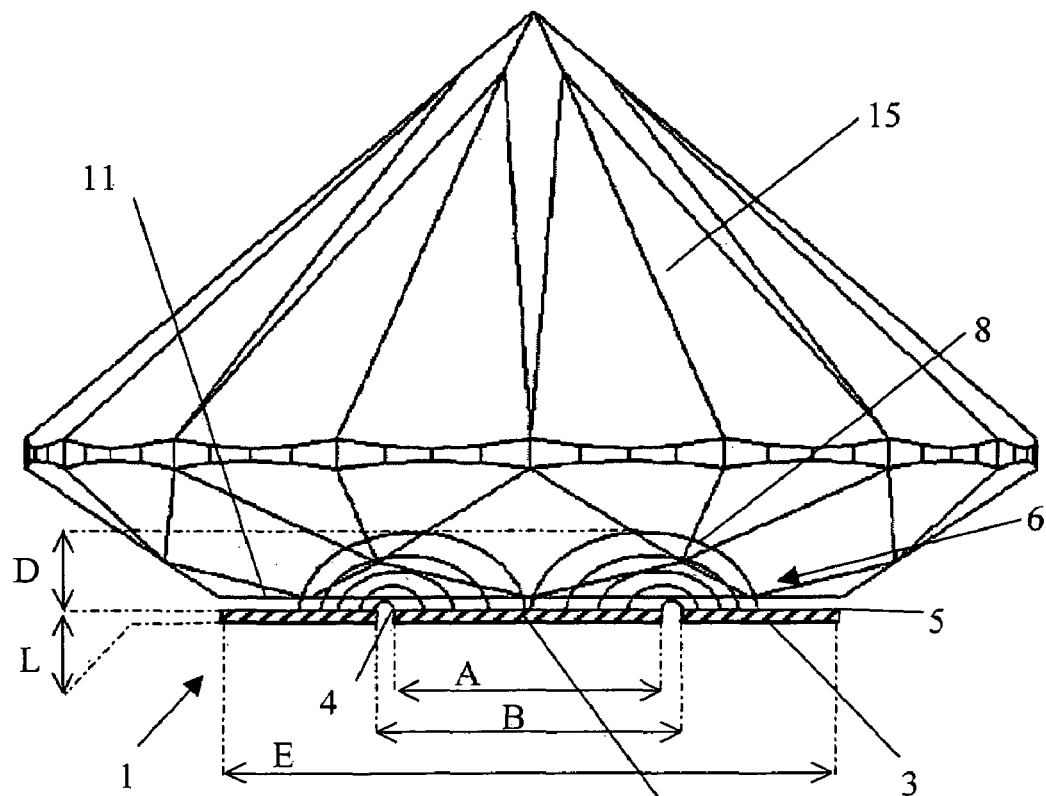
FIG. 2 is a schematic cross section of the top edge of a capacitive measuring probe with a gemstone made of a natural diamond.
Figure 3:
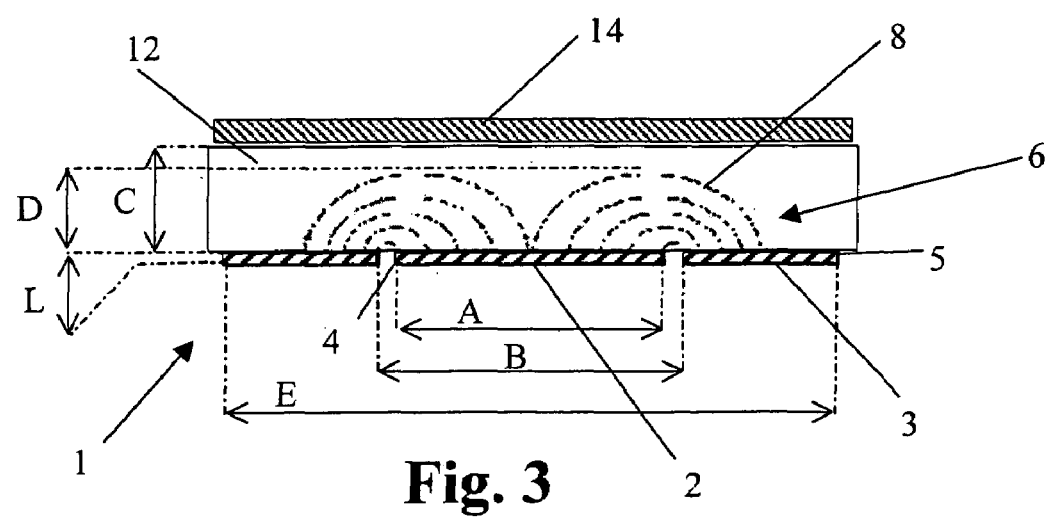
FIG. 3 is a schematic cross section of the top edge of a capacitive measuring probe with reference material in the electrical stray field of the measuring probe.

According to the method of the invention, a gemstone 15, 16, 17 is qualified by measuring the capacity of the capacitor of the measuring probe 1 after the gemstone 15, 16, 17 has been brought in the active electrical stray field 6, as represented in FIG. 2.

To this end, in order to qualify a cut gemstone 15, 16, 17, a facet 11 thereof is placed above the concentric cylinders 2 and 3 in the electrical stray field 6. The gemstone 15, 16, 17 must not necessarily make electrical contact with the electrodes 2 and 3 of the measuring probe 1. The flux lines 8 of the electrical stray field 6 run through the gemstone 15, 16, 17 and are influenced by the inner conductivity of the gemstone 15, 16, 17.

A measuring value of the capacity of the capacitor of the measuring probe 1 is thus obtained which depends on the inner conductivity of the gemstone 15, 16, 17.

According to the method of the invention, the measured capacity of the measuring probe 1, when said gemstone 15, 16, 17 is situated in its stray field 6, is compared to a reference capacity. This reference capacity is equal to the capacity of the measuring probe when a reference material having a higher dielectric constant than most solid matters is placed in the electrical stray field 6. When the measured capacity of the capacitor of said measuring probe 1 containing the gemstone 15, 16, 17 to be qualified, is larger than said reference capacity, this gemstone will be qualified as a gemstone with electrical conductivity qualities.

In order to determine this reference capacity, the measuring probe 1 is covered with electrically insulating reference material 12. Preferably, the reference material 12 will cover the total measuring surface of the measuring probe 1. The measuring surface of the measuring probe 1, on the side where the active electrical stray field 6 is situated, is limited by the edge 5 of the outer electrode 3. The reference material 12 has a specific dielectric constant of $\in_{r\_ref}$ which is larger than 9.7 and preferably smaller than 15.

The capacity of the capacitor of the measuring probe 1 is measured in the presence of the reference material 12. This measured capacity is taken as the reference capacity.

The thickness C of the reference material 12 is selected such that the electrical stray field 6 is at least entirely surrounded by it and, consequently, it is at least equal to the height D of this electrical stray field 6. When the thickness C of the reference material 12 is sufficient, the measured capacity of the measuring probe 1 or the reference capacity will not change when a conductive material 14 is provided on the side of the reference material 12 turned away from the measuring surface, since this conductive material 14 is situated outside the active stray field 6.

Figure 4:
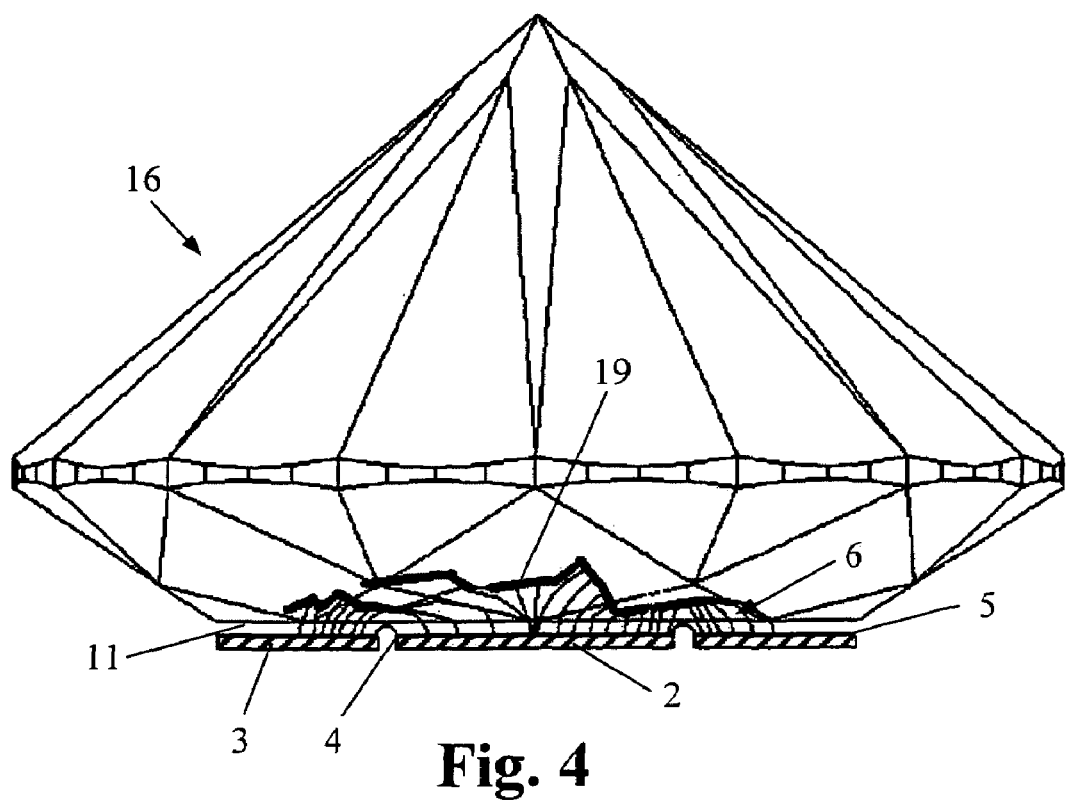
FIG. 4 is a schematic cross section of the top edge of a capacitive measuring probe whereby a gemstone with electrical conductivity qualities is situated in the electrical stray field of the measuring probe.

When a non-conductive gemstone 15, such as a natural diamond, having a dielectric constant $\in_r$ which is smaller than $\in_{r\_ref}$ is placed against the measuring surface of the capacitive probe 1, as represented in FIG. 4, the measured capacity value will be smaller than the reference capacity.

FIG. 4 represents a gemstone 16 which is placed against the measuring surface of a capacitive measuring probe 1. This gemstone 16 has inner fractures 19 containing for example graphite. Because of the presence of these fractures 19 in the stray field 6 of the measuring probe 1, the capacity of the capacitor of the measuring probe which is thus measured will be larger than said reference capacity. Hence, from this measurement can be concluded that the gemstone 16 has an electrical conductivity.

Figure 5:
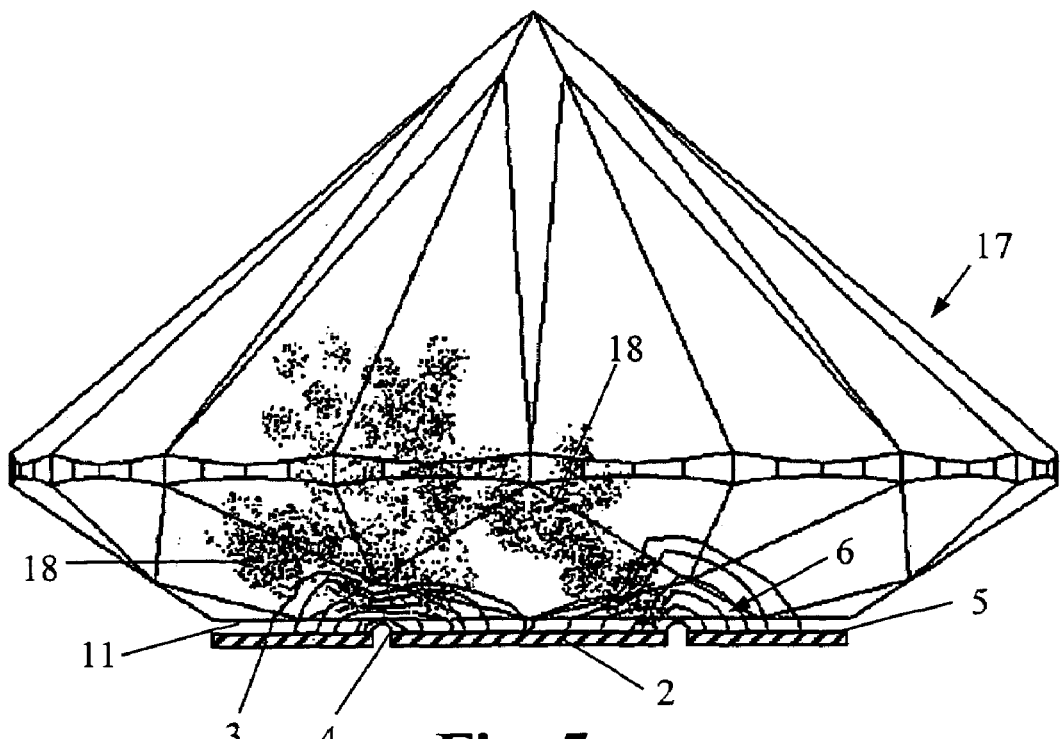
FIG. 5 is a representation analogous to that in FIG. 4, whereby a gemstone which is electrically conductive on the inside is situated in the electrical stray field of the measuring probe.

FIG. 5 represents a gemstone 17 with internal zones 18 which are electrically conductive. When these zones 18 are within the measuring range of the capacitive probe 1, the field lines 8 will be influenced such that the capacity of the measuring probe becomes larger than the reference capacity, such that it can also be concluded that the measured gemstone has electrical conductivity qualities.

It is not necessary for these measurements to cover the total measuring surface of the capacitive probe 1 with a facet 11 of the gemstone 15; 16 or 17. Nor must the volume described by the active field lines 8 be entirely occupied by the gemstone 15, 16 or 17. The electrical conductivity of the gemstone to be measured must not necessarily be a bulk characteristic. Thus, the electrical conductivity can be restricted for example to local electrically conductive zones in order to allow for a detection thereof. Nor is it required for these zones to be homogenously spread over the gemstone 16 or 17.

According to the method of the invention, a non-conductive diamond, such as type I diamonds and most type IIa diamonds, can for example be easily discerned from moissanite which is either or not diamond-coated.

In order to allow for a standardised measurement, the diameter E of the capacitive probe 1 is selected such that the measuring surface can be entirely covered by a facet 11, usually the table facet, of the gemstone 15, 16 or 17.

Electrode diameters E of 1 mm and more can be used. In the case of measuring probes with smaller diameters E, which are suitable for gemstones with small dimensions, the active field lines 8 close near the measuring surface, and the detection depth D amounts to a few tenths of a millimetre. In the case of measuring probes 1 with larger diameters E, detection depths D of a few millimetres are possible.

Naturally, the invention is not restricted to the above-described method and the device represented in the accompanying figures.

Thus, for the capacitive measuring probe 1, instead of a capacitor formed of cylindrical electrodes, also a capacitor consisting of coaxial, beam-shaped electrodes can be used, or any capacitor whose electrical stray field can be influenced by a conductive object.

Further, the measuring probe can be provided with an electrical shield, as a result of which the active field lines will be restricted to the space above the electrodes, and as a result of which fringes in the active field lines are avoided.

Thus, it is possible to qualify a gemstone which is set for example in a jewel which is electrically conductive without the measured capacity being influenced by the proximity of electrically conductive metals of the jewel.

The device for qualifying gemstones comprises, for example, a measuring probe, an oscillator and a detector. The oscillator is hereby tuned such that it will either or not oscillate at the reference capacity. As a function of the selected working principle of the oscillator, the detector will tell the user whether the capacity is situated above or under the reference capacity. Consequently, given the selected reference capacity, said influence can be attributed to the electrical conductivity qualities of the gemstone that is to be qualified.

The presence of an electrically conductive surface or of electrical conductivity qualities reaching up to the surface of a gemstone can also be discerned from electrical conductivity qualities which do not reach up to the surface. When the gemstone is placed against the electrodes of the capacitor of the measuring probe, these are bridged by the surface resistance of the gemstone. This results in a conduction current which can be discerned from the displacement current. It is hereby clear that the facet must be sufficiently large in order to cover the measuring surface of the electrodes.

Any common method for determining capacities can be used in order to determine whether the capacity of the capacitor of the measuring probe containing a gemstone is larger or smaller than the reference capacity. The arrangement can be made such that the reference capacity, via the set limitation of the measurement converter, is situated outside the range of the measurement converter.

According to a variant of the preceding method of the invention, diamond is taken as said reference material. When the capacity of said capacitive measuring probe is thus measured when it is placed against a facet of a gemstone to be qualified, and it is found that this capacity is larger than the reference capacity that was measured for diamond, one may conclude with much probability that the gemstone has a larger electrical conductivity than the diamond that is used as reference material. One must hereby take into account that the difference between the capacity that was measured in said gemstone and the reference capacity not only depends on the electrical conductivity qualities of the gemstone, but also on its dielectric constant. Consequently, if the measured capacity deviates more than, for example, five percent from the reference capacity, this means that the gemstone has electrical conductivity qualities and/or has another dielectric constant than the reference material. Thus, one may conclude that the gemstone is not made of the same material as the reference material.

The invention claimed is:

1. Method for qualifying gemstones by discerning gemstones from one another on the basis of their electrical conductivity, comprising:
   (i) placing at least a part of a gemstone (15,16,17) that is to be qualified in the electrical stray field of a capacitor;
   (ii) measuring the electrical capacitance of the capacitor;
   (iii) comparing the measured capacitance to a reference capacitance of this capacitor when a reference material (12) is placed in the electrical stray field, the reference material (12) having a dielectric constant which is smaller than 15 and larger than that of the gemstone (15,16,17) to be qualified, and
   (iv) qualifying the gemstone (15,16,17) as a gemstone with electrical conductivity when the capacitance of said capacitor, measured when said part of the gemstone (15,16,17) is in the stray electric field, is larger than said reference capacitance.

2. Method according to claim 1, wherein said reference material (12) has a dielectric constant which is at least equal to that of diamonds.

3. Method according to claim 1, wherein, in order to measure said reference capacitance, the reference material (12) has a relative dielectric constant which is larger than 9.7.

4. Method according to claim 1, wherein, in order to measure said capacitance, or said reference capacitance, said part of the gemstone (15,16,17) to be qualified, or said reference material (12) respectively, is placed within the measuring range of a capacitive measuring probe (1).

5. Method according to claim 4, wherein the measuring probe (1) comprises two concentric cylinders (2,3) made of an electrically conductive material, each cylinder having an edge, and wherein the gemstone (15,16,17) to be qualified or said reference material (12) is placed in the electrical stray field (6) formed on the edges (4,5) of said cylinders (2,3).

6. Method according to claim 4, wherein the measuring probe (1) comprises two coaxial electrodes (2,3), each with a polygonal section and each having an edge, and wherein the gemstone (15,16,17) to be qualified, or said reference material (12), is placed in the electrical stray field (6) formed on the edges (4,5) of said electrodes (2,3).

7. Method according to claim 1, wherein said capacitance is measured via at least one facet (11) of the gemstone (15,16,17) to be qualified.

8. Method according to claim 1, wherein said capacitor has electrodes and said gemstone (15,16,17) to be qualified is electrically insulated in relation to the electrodes (2,3) of said capacitor.

9. Method according to claim 1, wherein said capacitor is provided with a shield in order to prevent its capacitance from being influenced by electrically conductive parts of a jewel in which the gemstone (15,16,17) to be qualified is set.

10. Method according to claim 1, wherein diamond is used as said reference material (12).

11. Device for qualifying gemstones by discerning gemstones from one another on the basis of their electrical conductivity, said device comprising:

a capacitor producing an electrical stray field and in which at least a part of a gemstone (15,16,17) to be qualified can be placed;

a measurement converter (9) for generating a signal as a function of the capacitance of said capacitor when at least the part of the gemstone to be qualified is placed in the electrical stray field of the capacitor;

a read-out unit (10) for displaying said signal; and means for generating a signal when the measured capacitance for the gemstone (15,16,17) to be qualified, placed in said electrical stray field, is larger than a reference capacitance value in relation to which this device is calibrated and which is at least equal to the capacitance value of said capacitor when a reference material (12) is placed in said electrical stray field, said reference material (12) having a dielectric constant which is smaller than 15 and larger than that of the gemstone (15,16,17) to be qualified.

12. Device according to claim 11, wherein said device is calibrated in relation to a reference capacitance value that is at least equal to the capacitance value of said capacitor when a material with a dielectric constant that is larger than that of diamonds is placed in the electrical stray field of this capacitor.

13. Device according to claim 11 or 12, wherein said capacitor comprises a capacitive measuring probe (1).

14. Device according to claim 11 or 12, wherein said capacitor has electrodes, and further comprising an electrical isolator provided between the gemstone (15,16,17) to be qualified and the electrodes (2,3) of said capacitor.

15. Device according to claim 11 or 12, wherein said capacitor comprises a shield in order to prevent its capacitance from being influenced by electrically conductive parts of a jewel in which the gemstone (15,16,17) to be qualified is set.

* * * * *